(12) United States Patent
Janas

(10) Patent No.: US 10,227,554 B2
(45) Date of Patent: Mar. 12, 2019

(54) DEVICES, METHODS AND SYSTEMS FOR COLLECTING WASTE FROM A BIOREACTOR

(71) Applicant: GE HEALTHCARE UK LIMITED, Chalfont St. Giles, Buckinghamshire (GB)

(72) Inventor: Michelle Louise Janas, Cardiff (GB)

(73) Assignee: GE Healthcare UK Limited, Buckinghamshire (GB)

(*) Notice: Subject to any disclaimer, the term of this patent is extended or adjusted under 35 U.S.C. 154(b) by 0 days.

(21) Appl. No.: 15/529,567

(22) PCT Filed: Dec. 15, 2015

(86) PCT No.: PCT/EP2015/079777
§ 371 (c)(1),
(2) Date: May 25, 2017

(87) PCT Pub. No.: WO2016/096845
PCT Pub. Date: Jun. 23, 2016

(65) Prior Publication Data
US 2017/0335267 A1 Nov. 23, 2017

(30) Foreign Application Priority Data
Dec. 18, 2014 (GB) .................................. 1422665.8

(51) Int. Cl.
*C12M 1/00* (2006.01)
(52) U.S. Cl.
CPC ............ *C12M 23/34* (2013.01); *C12M 23/14* (2013.01); *C12M 29/00* (2013.01); *C12M 47/00* (2013.01); *C12M 47/16* (2013.01)
(58) Field of Classification Search
CPC ........ C12M 21/00–21/18; C12M 23/00–23/58
See application file for complete search history.

(56) References Cited

U.S. PATENT DOCUMENTS

| 6,224,571 B1 * | 5/2001 | Bierman | A61M 25/02 604/174 |
| 6,685,684 B1 * | 2/2004 | Falconer | A61F 5/441 604/332 |
| 8,343,120 B2 * | 1/2013 | Smith | A61F 5/448 156/254 |

FOREIGN PATENT DOCUMENTS

| EP | 2141226 A1 | 1/2010 |
| GB | 2351442 A | 1/2001 |

(Continued)

OTHER PUBLICATIONS

PCT International Search Report and Written Opinion for PCT Application No. PCT/EP2015/079777 dated Mar. 15, 2016 (8 pages).

*Primary Examiner* — Janine M Kreck
(74) *Attorney, Agent, or Firm* — Eversheds Sutherland (US) LLP

(57) ABSTRACT

The invention relates to devices, methods and systems for collecting and solidifying waste material from bioreactor cell cultures in order to facilitate waste disposal. The invention finds particular utility in mammalian cell culture applications. A transverse wall divides the interior of a waste bag into two chambers, the first chamber containing an inlet receiving waste liquid from a bioreactor, the second chamber containing an absorbent material to solidify the liquid into a gel. The transverse wall acts to direct the flow of waste media into the second chamber where it is converted into a gel and further prevents the inlet from being blocked by any gel or particulate materials. Methods and uses regarding this invention are described.

17 Claims, 3 Drawing Sheets

(56) References Cited

FOREIGN PATENT DOCUMENTS

| GB | 2458477 A | * | 9/2009 | ........... A61F 5/4404 |
|----|-----------|---|--------|------------------------|
| WO | 97/43988 A1 | | 11/1997 | |
| WO | 2006/107843 A1 | | 10/2006 | |

* cited by examiner

DEVICES, METHODS AND SYSTEMS FOR COLLECTING WASTE FROM A BIOREACTOR

CROSS REFERENCE TO RELATED APPLICATIONS

This application claims the priority benefit of PCT/EP2015/079777 filed on Dec. 15, 2015 which claims priority benefit of Great Britain Application No. 1422665.8 filed Dec. 18, 2014. The entire contents of which are hereby incorporated by reference herein.

TECHNICAL FIELD OF THE INVENTION

The invention relates to devices, methods and systems for collecting waste materials from bioreactor cell cultures. The invention finds particular utility in the production of cells for mammalian cell culture applications.

BACKGROUND TO THE INVENTION

Bioreactors are commonly used to culture cells under optimal temperatures and conditions to promote growth. Examples of bioreactors include Xuri™ W5 (GE Healthcare), Xuri™ W25 (GE Healthcare), WAVE Bioreactor™ (GE Healthcare) and stir-tank bioreactors. Liquid growth media is often used to feed the cells by supplying them with nutrients, sugars and growth factors necessary to promote growth, expansion and/or differentiation. As the cells grow and divide they utilise these nutrients and often excrete metabolites which can be toxic to the cells. The used, spent or waste media must therefore be removed and the cells fed with fresh media to continue to promote their growth and expansion.

The removal and/or disposal of this waste media can present problems as it often requires opening the cell culture to decant the waste media thus exposing the culture to potential contamination from airborne microbes. Once collected, the liquid waste must be sterilised, typically by autoclaving, before it can be disposed of. This sterilisation process is time consuming and labour intensive. Alternatively, the liquid waste may be solidified and then disposed of by incineration.

In a typical cell culture system there are three main liquid reservoir components a cell bag in which cells are cultured; a media bag which stores and supplies fresh media into the cell bag; and a waste bag in which used media and waste from the cell bag is collected. The waste bag may need to be detached and replaced several times during the culture process, exposing the cell culture to airborne microbes and risking contamination of the final cell product. This waste is then decanted into a separate container for autoclaving or liquid solidification prior to disposal.

The use of gelling agents to convert liquid waste into solid form for ease of disposal is known in the art. For example, U.S. Pat. No. 5,807,230 discloses waste disposal devices for minimising contamination of an operating room table with blood and body fluid run-off. The bags may contain gelling agents for solidifying the waste material for ease of subsequent disposal.

US2005455972A provides a disposal waste bag containing an absorbent material in a pouch, patch bonded or glued to the bag, or as crystals.

GB2351442A (Smiths Industries Public Limited Company) describes a chest drainage bag with an absorbent material capable of converting the waste flowing from the inlet into a solid. GB2351442A provides an internal member which is a flap extending across the width of the bag, welded at spaced intervals to a wall of the bag. Through the movement of the member in a lever-like motion, liquid travels towards an absorbent material where it is solidified. This member then hinders movement of the solid material back towards the inlet. However, it is cumbersome and expensive to manufacture this chest drainage bag due to the separate welds required to weld the wall to the bag.

EP1736183B1 (VacSax Limited) describes a medical suction disposal system with a flexible body in which liquid from the waste bag of a bioreactor is decanted. The process of decanting into such a system, however, is time consuming and purchasing the system incurs extra cost. Furthermore, the body of this disposal system is not space efficient. However, without VacSax, the waste liquid in the waste bag would need to be autoclaved.

An absorbent material can, additionally, be placed into such a VacSax disposal system in order to solidify the waste before the system is incinerated. Suitable absorbent materials can, for example, be purchased separately from VacSax: (http://www.vacsax.co.uk/index.php/products/-PreGel Gelling Agent) and placed in the system; alternatively the disposal system is also available containing the absorbent material.

In the field of cell culture, there is therefore a need for devices, methods and systems which provide cost-effective and efficient methods for waste collection and disposal which minimise the risk of contamination of the final cell product. The present invention addresses these problems and provides devices, methods and systems which are easy to manufacture and use and further enable collection, solidification and subsequent disposal of waste from a bioreactor.

SUMMARY OF THE INVENTION

According to the first aspect of the present invention, there is provided a bioreactor waste bag comprising: an outer wall and an inner wall enclosing an interior within; a transverse wall dividing the interior into a first and second chamber in fluid communication there-between; the first chamber comprising an inlet connectable to a bioreactor; the second chamber comprising an absorbent material which is capable of converting liquid into a gel; and wherein the transverse wall extends above the inlet to prevent blockage thereof by the absorbent material or the gel.

As used herein, the word "gel" is meant to include semi-solid colloidal suspensions and jellies.

In one embodiment, the transverse wall extends more than half the height of the bag. Preferably, the transverse wall extends to three quarters the height of the bag.

In another embodiment, the bag further comprises a connector line connectable to a bioreactor. Such connector line should be biologically inert and sterilisable.

In a further embodiment, the connector line further comprises of a leur lock connectable to a bioreactor for sterile connection to the bioreactor.

In one embodiment, the inlet has a single port connector connectable to the connector line. This port connector facilitates sterile connection to the connector line using a sterile welding device, such as that available from Terumo (TSCD® II Sterile Tubing Welder) (http://www.terumobct-.com/location/emea/products-and-services/Pages/TSCD-II.aspx).

In another embodiment, the connector line may be made from sterilisable ⅛" clinical grade c-flex plastic or poly vinyl chloride which is sterilisable and biologically inert.

In a further embodiment, the bag comprises a bacterial filter to allow sterile gas exchange between the interior and exterior of the bag. The use of such a filter reduces the risk of microorganisms entering and contaminating the bioreactor and enables excess gas to be released.

In one embodiment, the absorbent material is located in the base of the bag.

In another embodiment, said absorbent material is a superabsorbent polymer. Sodium polyacrylate is by far the most common superabsorbent polymer for absorbing waste liquid but other, non-limiting examples, include polyacrylamide copolymer, ethylene maleic anhydride copolymer, cross-linked carboxymethylcellulose, polyvinyl alcohol copolymers, cross-linked polyethylene oxide and starch grafted copolymer of polyacrylonitrile.

In a further embodiment, said absorbent material is provided as crystals, in a sachet, on a patch or impregnated in an internal wall of the second chamber. Where a sachet or patch is used, the membranes are easily dissolvable.

In one embodiment, the outer wall and/or the inner wall is composed of a material selected from the group consisting of poly vinyl chloride, polyethylene, ethylene vinyl acetate and ethylene vinyl alcohol.

In another embodiment, the bag is sterilisable, for example by gamma radiation.

In a further embodiment, the bag comprises a handle which provides for ease of use.

According to a second aspect of the present invention, there is provided a method of collecting waste media from a bioreactor into a waste bag, the waste bag comprising an outer wall and an inner wall enclosing an interior within;
a transverse wall dividing the interior into a first and second chamber in fluid communication there-between;
the first chamber comprising an inlet connectable to a bioreactor;
the second chamber comprising an absorbent material which is capable of converting liquid into a gel; and
wherein the transverse wall extends above the inlet (8) to prevent blockage thereof by the absorbent material;
the method comprising the steps of collecting waste media from a bioreactor in the waste bag and converting the media into a gel.

In one embodiment, the method additionally comprises disposing of the bag, thereby reducing the need to transfer the material to a separate waste container.

According to a third aspect of the present invention, there is provided a use of a bag as herein described for collecting waste media from a bioreactor.

According to a fourth aspect of the present invention, there is provided a system comprising a bag as herein before described connected to a bioreactor.

The bioreactor waste bag, its method of use and systems comprising can be used with any biological cells that can be grown in culture such as microbial, plant, viral and animal cells. In particular, mammalian cells and preferably human cells. Examples of mammalian cells that may be used in the present invention include but are not limited to blood cells, such as red blood cells (erythrocytes), white blood cells (including leukocytes, lymphocytes, granulocytes and monocytes), platelets (thrombocytes) and stem cells (for example, embryonic, adult, induced pluripotent and hematopoietic stem cells).

DETAILED DESCRIPTION OF THE DRAWINGS

Figure 1:
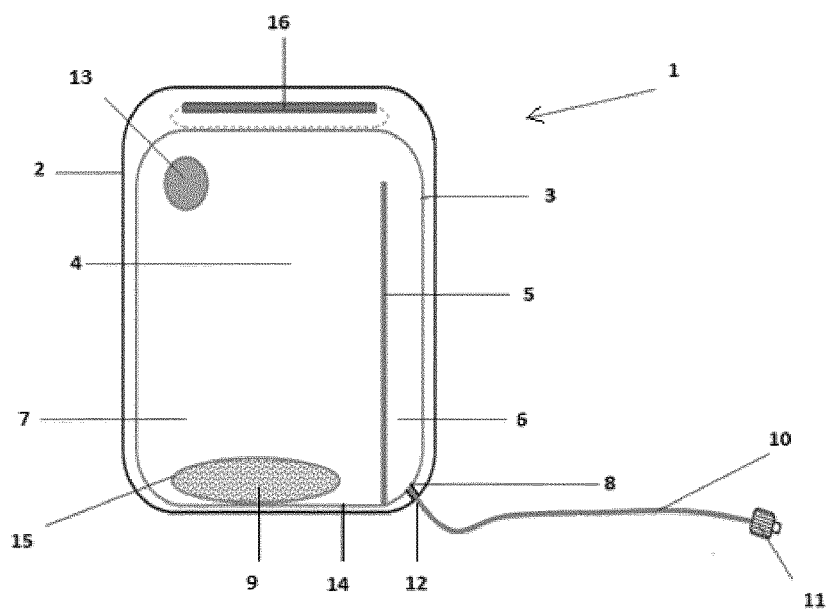
FIG. 1 is a schematic illustration of a front perspective of a bioreactor waste bag according to the invention.

FIG. 1 illustrates the waste bag (1) of the invention connected to a bioreactor (not shown) prior to release of waste media into the bag (1). The rectangular waste bag (1) consists of outer (2) and inner (3) walls which may be composed of any suitable inert, sterilisable polymer such as poly vinyl chloride, polyethylene, ethylene vinyl acetate or ethylene vinyl alcohol. The interior (4) of the bag is divided into first (6) and second (7) chambers by a transverse wall (5), the chambers (6, 7) being in fluid communication with each other. The first chamber (6) has an inlet (8) connected to a connector line (10) via a single port connector (12) and receives waste liquid from a bioreactor (not shown) connected via a locking tip such as a male leur lock (11). The connector line (10) may be made from an inert polymer such as clinical grade c-flex plastic or poly vinyl chloride. In the example shown, the second chamber (7) contains a sachet (15) with a soluble packaging which contains an absorbent material (9) which absorbs liquid waste solidifying it for subsequent, direct incineration. Examples of suitable absorbent materials include PreGel Gelling Agent available from VacSax (http://www.vacsax.co.uk/index.php/products/))

The transverse internal wall (5) rises upwards from the base (14) of the bag (1) and extends to approximately three quarters of the height of the bag (1), defining the two chambers. The purpose of the transverse internal wall (5) is to direct liquid flow unidirectionally over the internal wall (5) itself and towards the sachet (15) of absorbent material (9) in the second (7) chamber where the liquid solidifies into a gel. The internal wall (5) is also designed to prevent the gel from blocking the inlet (8) as it acts as a partition. A gas vent/filter (13), such as a bacterial filter, enables gas exchange and prevents microbial contamination. A handle (16) is provided for portability, ease of use and suspension of the bag (1) next to the bioreactor.

The bag (1) may be designed to accommodate five liters (5 L) of liquid waste and other bags can accommodate higher and lower volumes, for example, one to twenty five liters (1-25 L).

Figure 2:
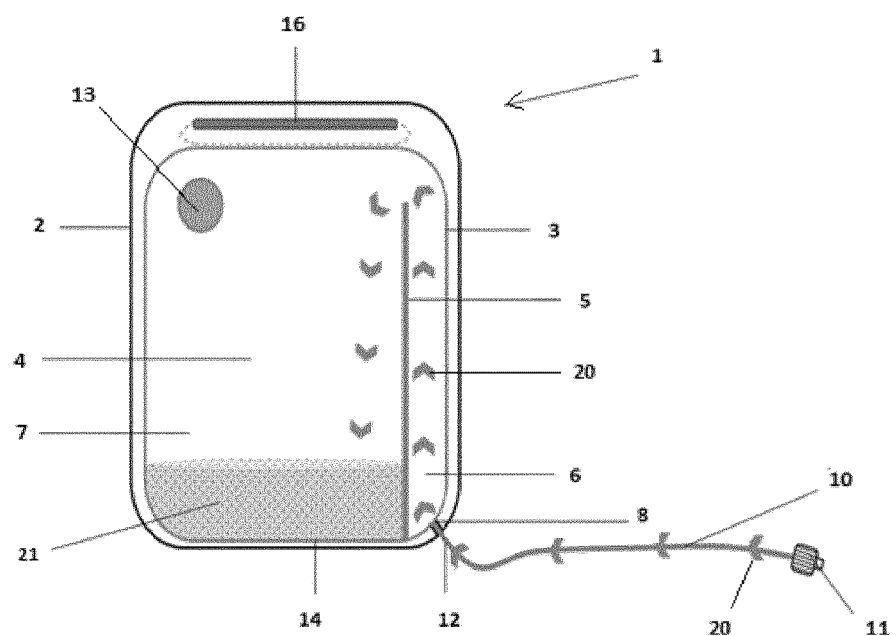
FIG. 2 is a schematic illustration of a front perspective of the bioreactor waste bag of FIG. 1 highlighting the direction of flow of waste media.

FIG. 2 illustrates waste media flow from the bioreactor (not shown) entering the bag (1) of FIG. 1. The arrowheads (20) illustrate the direction of flow of the waste media from the bioreactor into the bag (1).

The transverse wall (5) rises upwards from the base (14) of the bag (1) and, in the embodiment shown, extends to approximately three quarters of the height of the bag thereby dividing the interior (4) into two chambers (6, 7). The transverse wall (5) guides liquid flow from the inlet (8), over the transverse wall (5) and towards the absorbent material (FIG. 1, feature (9)) in the second chamber (7) (as indicated by the arrowheads (20)). The sachet of absorbent material (FIG. 1, features 15 and 9) in the base (14) of the bag, which is typically made of a soluble material such as polyvinyl alcohol, dissolves on contact with the waste media to release the absorbent material (FIG. 1, feature (9)) which then reacts with the media to form a gel.

The gel is shown as a layer (21) in the figure.

The transverse wall (5) is also designed to prevent the backward flow of gel (21) or particulate material from blocking the inlet (8) as it acts as a partition.

In this way, the waste from the bioreactor can be directly solidified into a gel in the waste bag and subsequently disposed of by way of incineration.

Figure 3:
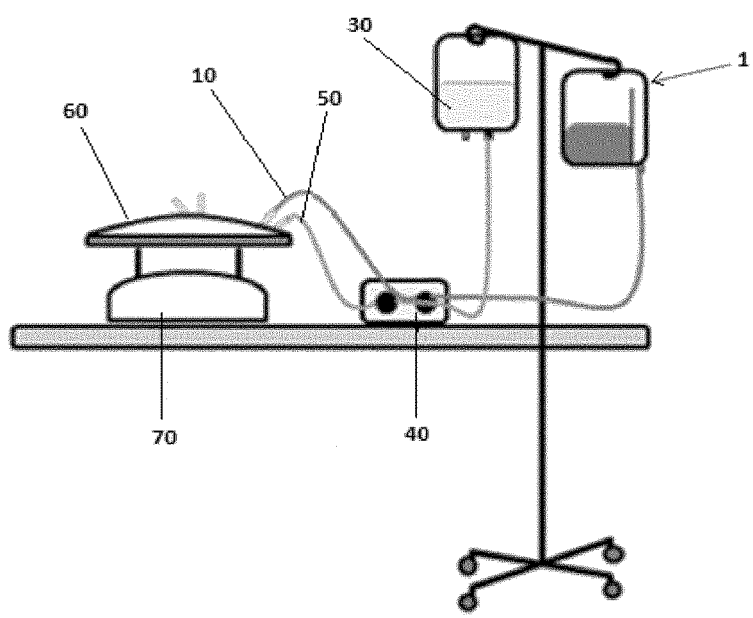
FIG. 3 is a schematic illustration of a system in accordance with the invention.

FIG. 3 illustrates a system according to the present invention in which the waste bag (1) of FIG. 1 is attached to bioreactor (60) via a pump unit (40). The feed-in line (50) directs cell media from the media bag (30) towards the bioreactor (60), while the connector line (10) takes waste away from the bioreactor (60) towards the waste bag (1). The bioreactor is supported on a base (70) which may optionally be used to agitate the bioreactor to facilitate growth of the cells.

While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

The invention claimed is:

1. A bioreactor waste bag comprising:
   an outer wall and an inner wall enclosing an interior having a base;
   a fluid-impermeable transverse wall partially dividing said interior into a first chamber and a second chamber in fluid communication thereover;
   the first chamber comprising an inlet connectable to a bioreactor;
   the second chamber comprising an absorbent material which is capable of converting liquid into a gel; and
   wherein the transverse wall extends upwards from the base above the inlet to prevent blockage thereof by said absorbent material or said gel.

2. The bag according to claim 1, wherein said transverse wall extends more than half the height of the bag.

3. The bag according to claim 1, further comprising a connector line connectable to a bioreactor.

4. The bag according to claim 3, wherein the connector line further comprises of a luer lock connectable to a bioreactor.

5. The bag according to claim 3, the inlet has a single port connector connectable to the connector line.

6. The bag according to claim 3, wherein the connector line may be composed of clinical-grade c-flex plastic or poly vinyl chloride.

7. The bag according to claim 1, further comprising a bacterial filter to allow sterile gas exchange between the interior and exterior of the bag.

8. The bag according to claim 1, wherein said absorbent material is located in the base of the bag.

9. The bag according to claim 1, wherein said absorbent material is a superabsorbent polymer.

10. The bag according to claim 1, wherein said absorbent material is provided in a sachet, on a patch, as crystals or impregnated in an internal wall of the second chamber.

11. The bag according to claim 1, wherein the outer wall and/or the inner wall is composed of a material selected from the group consisting of poly vinyl chloride, polyethylene, ethylene vinyl acetate and ethylene vinyl alcohol.

12. The bag according to claim 1, that is sterilisable.

13. The bag according to claim 1, additionally comprising a handle.

14. A method of collecting waste media from a bioreactor waste bag, said waste bag comprising:
   an outer wall and an inner wall enclosing an interior within;
   a transverse wall dividing said interior into a first and second chamber in fluid communication there-between;
   the first chamber comprising an inlet connectable to a bioreactor;
   the second chamber comprising an absorbent material which is capable of converting liquid into a gel; and
   wherein the transverse wall extends above the inlet to prevent blockage thereof by said absorbent material or said gel;
   said method comprising the steps of collecting waste media from a bioreactor in the waste bag and converting said media into a gel.

15. The method according to claim 14, additionally involving the step of disposing of said bag.

16. A method of collecting waste media from a bioreactor waste bag comprising collecting the waste media in the second chamber of the bag according to claim 1.

17. A system comprising a bioreactor waste bag connected to a bioreactor, wherein the bioreactor waste bag comprises:
   an outer wall and an inner wall enclosing an interior having a base;
   a transverse wall partially dividing said interior into a first chamber and a second chamber in fluid communication thereover;
   the first chamber comprising an inlet connectable to a bioreactor;
   the second chamber comprising an absorbent material which is capable of converting liquid into a gel; and
   wherein the transverse wall extends upwards from the base above the inlet to prevent blockage thereof by said absorbent material or said gel.

* * * * *